United States Patent [19]

McCully

[11] Patent Number: 4,925,931

[45] Date of Patent: May 15, 1990

[54] N-HOMOCYSTEINE THIOLACTONYL RETINAMIDO COBALAMIN AND METHODS OF USE THEREOF

[76] Inventor: Kilmer S. McCully, 15 Wildwood St., Winchester, Mass. 01890

[21] Appl. No.: 219,499

[22] Filed: Jul. 14, 1988

[51] Int. Cl.$^5$ .................. C07H 19/167; C07D 333/20; A61K 31/365; A61K 31/38
[52] U.S. Cl. ........................................ 536/25; 435/86; 514/52; 549/29
[58] Field of Search .............. 536/25; 514/52; 549/29; 435/86

[56] References Cited

U.S. PATENT DOCUMENTS

| | | | |
|---|---|---|---|
| 4,255,443 | 3/1981 | McCully | 424/275 |
| 4,364,939 | 12/1982 | Aurissier et al. | 424/180 |
| 4,383,994 | 5/1983 | McCully | 424/245 |
| 4,465,775 | 8/1984 | Houts | 436/503 |
| 4,618,685 | 10/1986 | McCully | 549/63 |

OTHER PUBLICATIONS

F. G. Arsenyan et al., "Influence of Methylcobalamin on the Antineoplastic Activity of Methotrexate," *Khimiko-Farmatsevticheskii Zhurnal*, vol. 12, (1978), pp. 1299–1303 (translation).
P. Boerner et al., "Methionine-Sensitive Glycolysis in Transformed Cells," *Proc. Natl. Acad. Sci. U.S.A.*, vol. 82, (1985), pp. 6750–5764.
R. Gaggi et al., "The Role of Homocysteine in the Pathogenesis of Arteriosclerosis," proceedings of the First Congress of the Hungarian Pharmacological Society (Budapest), vol. 2, (1973), pp. 287–297.
R. M. Hoffman, "Altered Methionine Metabolism, DNA Methylation and Oncogene Expression in Carcinogenesis," *Biochimica et Biophysica Acta*, vol. 738, (1984), pp. 49–87.
J. C. Linnell et al., "Altered Cobalamin Distribution in Rat Hepatomas and in the Livers of Rats Treated with Diethylnitrosamine," *Cancer Research*, vol. 37, (1977), pp. 2975–2978.
K. S. McCully et al., "Production of Arteriosclerosis by Homocysteinemia," *Am. J. Pathology*, vol. 61, (1970), pp. 1–11.
K. S. McCully et al., "Homocysteine Theory of Arteriosclerosis," *Atherosclerosis*, vol. 22, (1975), pp. 215–227.
K. S. McCully et al., "Homocysteine Thiolactone Metabolism in Malignant Cells," *Cancer Research*, vol. 36, (1976), pp. 3198–3202.
K. S. McCully et al., "Homocysteine Compounds Which Influence the Growth of a Malignant Neoplasm," *Chemotherapy*, S. Karger, Basel, vol. 23, (1977), pp. 44–49.
K. S. McCully et al., "Antineoplastic Activity of a Rhodium Trichloride Complex of Oxalyl Homocysteine Thiolactone," *Cancer Investigation*, vol. 5, (1987), pp. 25–30.
K. S. McCully et al., "Chemopreventive and Antineoplastic Activity of N-Homocysteine Thiolactonyl Retinamide," *Carcinogenesis*, vol. 8, (1987), pp. 1559–1562.
K. S. McCully et al., "Homocysteine Thiolactone, N-Homocysteine Thiolactonyl Retinamide, and Platelet Aggregation," *Research Communications in Chemical Pathology and Pharmacology*, vol. 56, (1987), pp. 349–360.
K. S. McCully et al., "Homocysteine Thiolactone in Arteriosclerosis and Cancer," *Research Communications in Chemical Pathology and Pharmacology*, vol. 59, (1988), pp. 107–119.

Primary Examiner—Johnnie R. Brown
Assistant Examiner—Gary L. Kunz
Attorney, Agent, or Firm—John S. Roberts, Jr.

[57] ABSTRACT

N-Homocysteine thiolactonyl retinamido cobalamin is useful for decreasing the induction of chemically-induced tumors in animals. It is also useful for inhibiting weight gain.

5 Claims, 2 Drawing Sheets

—— AdCob  —·— NHTR  ---- (NHTR)Cob

N-HOMOCYSTEINE THIOLACTONYL RETINAMIDO COBALAMIN AND METHODS OF USE THEREOF

TECHNICAL FIELD

This invention relates to N-homocysteine thiolactonyl retinamido cobalamin and its uses, including decreasing induction of chemically-induced tumors and inhibiting weight gain in animals.

BACKGROUND ART

The following references are cited:
F. G. Arsenyan et al., "Influence of Methylcobalamin on the Antineoplastic Activity of Methotrexate," *Khimiko-Farmatsevticheskii Zhurnal*, vol. 12 (1978), pages 1299–1303 (translation).
P. Boerner et al., "Methionine-sensitive glycolysis in transformed cells," *Proc. Natl. Acad. Sci. USA*, vol. 82 (1985), pages 6750–5764.
R. Gaggi et al., "The Role of Homocysteine in the Pathogenesis of Arteriosclerosis," Proceedings of the First Congress of the Hungarian Pharmacological Society (Budapest), vol. 2 (1973), pages 287–297.
R. M. Hoffman, "Altered Methionine Metabolism, DNA Methylation and Oncogene Expression in Carcinogenesis," *Biochimica et Biophysica Acta*, vol. 738 (1984), pages 49–87.
J. C. Linnell et al., "Altered Cobalamin Distribution in Rat Hepatomas and in the Livers of Rats Treated with Diethylnitrosamine," *Cancer Research*, vol. 37 (1977), pages 2975–2978.
K. S. McCully et al., "Production of Arteriosclerosis by Homocysteinemia," *Am. J. Pathology*, vol. 61 (1970), pages 1–11.
K. S. McCully et al., "Homocysteine Theory of Arteriosclerosis," *Atherosclerosis*, vol. 22 (1975), pages 215–227.
K. S. McCully et al., "Homocysteine Thiolactone Metabolism in Malignant Cells," *Cancer Research*, vol. 36 (1976), pages 3198–3202.
K. S. McCully et al., "Homocysteine Compounds which Influence the Growth of a Malignant Neoplasm," *Chemotherapy*, S. Karger, Basel, vol. 23 (1977), pages 44–49.
K. S. McCully, "Homocysteine Thiolactone Perchlorate as a Tumor Promotor," U.S. Pat. No. 4,255,443 (1981).
K. S. McCully, "Homocysteine Thiolacatone Salts and Use Thereof as Anti-neoplastic Agents," U.S. Pat. No. 4,383,994 (1983).
K. S. McCully, "N-Homocysteine Thiolactonyl Retinamide and Use Thereof as an Antineoplastic Agent," U.S. Pat. No. 4,618,685 (1986).
K. S. McCully et al., "Antineoplastic Activity of a Rhodium Trichloride Complex of Oxalyl Homocysteine Thiolactone," *Cancer Investigation*, vol. 5 (1987), pages 25–30.
K. S. McCully et al., "Chemopreventive and antineoplastic activity of N-homocysteine thiolactonyl retinamide," *Carcinogenesis*, vol. 8 (1987), pages 1559–1562.
K. S. McCully et al., "Homocysteine Thiolactone, N-Homocysteine Thiolactonyl Retinamide, and Platelet Aggregation," *Research Communications in Chemical Pathology and Pharmacology*, vol. 56 (1987), pages 349–360.
K. S. McCully et al., "Homocysteine Thiolactone in Arteriosclerosis and Cancer," *Research Communications in Chemical Pathology and Pharmacology*, vol. 59 (1988), pages 107–119.

McCully (1986; McCully et al. 1987, *Carcinogenesis*) has proposed using N-homocysteine thiolactonyl retinamide, obtained by reaction between trans-retinoic acid and homocysteine thiolactone free base, to reduce pulmonary tumor formation in A/J female mice, treated with tumor-inducing amounts of ethyl carbamate. N-Homocysteine thiolactone retinamide also inhibited the growth of transplanted MUO4 rhabdomyosarcoma in C57BL/6N male mice. N-Homocysteine thiolactone retinamide accordingly has antineoplastic and chemopreventive activity with respect to tumor growth in mice.

N-Maleyl homocysteine thiolactone amide, N-maleamide homocysteine thiolactone hydroperchlorate and rhodium trichloride oxalyl homocysteine thiolactone hydroperchlorate have been proposed as antineoplastic agents (McCully 1983; McCully et al. 1987, *Cancer Investigation*).

Homocysteine thiolactone perchlorate, however, has been found to promote tumor growth (McCully, 1981). The compound can be used to induce growth of malignant tumors in laboratory animals.

The effects of other homocysteine derivatives on the growth of malignant neoplasms have also been considered (McCully 1976; McCully et al. 1977, 1988).

Homocysteine and related compounds also affect arteriosclerosis (McCully et al. 1970, 1975, 1988; Gaggi et al. 1973). Homocysteine thiolactone and N-homocysteine thiolactonyl retinamide also influence platelet aggregation and may cause thombosis in human and experimentally-induced homocysteinemia (McCully et al. 1987, *Research Communications*).

Methionine is reported to inhibit glycolysis of Kirsten murine sarcoma virus-transformed rat kidney cells (Boerner et al. 1985).

Other reports correlating abnormal methionine metabolism with carcinogenesis are reviewed by Hoffman (1984).

Increased methylcobalamin concentration in tumors and livers of rats has been reported (Linnell et al. 1977). It has also been proposed that methylcobalamin stimulates growth of transplantable tumors in mice (Arsenayn et al. 1978).

It will therefore be appreciated that the relationship between homocysteine derivatives or cobalamin derivatives and growth of tumors is complex and that the subject is not understood well.

It is an object of this invention to provide a novel compound for inhibiting the growth of tumors. The compound surprisingly includes cobalamin, which is related to recognized tumor stimulants.

DESCRIPTION OF THE INVENTION

In one aspect, this invention relates to the novel compound N-homocysteine thiolactonyl retinamido cobalamin.

In a preparative aspect, this invention relates to a process for preparing homocysteine thiolactonyl retinamido cobalamin by reacting N-homocysteine thiolactonyl retinamide with 5'-deoxyadenosyl cobalamin.

In one method of use, this invention provides a method for decreasing the induction of chemically-induced tumors in animals, comprising administering to an animal being treated N-homocysteine thiolactonyl retinamido cobalamin, in admixture with a physiologically and pharmaceutically acceptable carrier, in an amount effective to decrease induction of tumors.

In a further method-of-use aspect, this invention relates to a method for inhibiting weight gain in animals, comprising administering to an animal being treated N-homocysteine thiolactonyl retinamido cobalamin, in admixture with physiologically and pharmaceutically acceptable carrier, in an amount effective to inhibit weight gain.

N-Homocysteine thiolactonyl retinamido cobalamin is made by reaction between N-homocysteine thiolactonyl retinamide and 5'-deoxyadenosyl cobalamin. The reaction can be represented by the equation:

$$2NHTR + AD\text{-}Cob \rightarrow (NHTR)_2Cob + Ad$$

wherein NHTR represents N-homocysteine thiolactonyl retinamide, Ad-Cob is 5'-deoxyadenosyl cobalamin, $(NHTR)_2Cob$ is 2:1 N-homocysteine thiolactonyl retinamido cobalamin, and Ad is 5'-deoxyadenosine.

NHTR can be made as recited by McCully '685, herein incorporated by reference. It will be appreciated that NHTR can include any possible stereoisomeric variations of the retinamide function. Various isomers of retinoic acid are described in M. Sporn et al., eds., "The Retinoids," volume 1, Academic Press, Orlando (1984), pages 399–403. However, N-homocysteine thiolactonyl retinamido cobalamin preferably is derived from all-trans retinoic acid.

5'-Deoxyadenosyl cobalamin is also known as coenzyme $B_{12}$, 5,6-dimethylbenzimidazolylcobamide 5'-deoxyadenosine, etc. The structure is given, for example, as entry no. 2407, "The Merck Index," Merck & Co., Rahway, N.J., M. Windholz et al., Eds., Tenth Edition (1983), page 348.

A preferred compound of the invention is one made by reaction between about two moles of NHTR and one more of Ad-Cob, so that the product is about $(NHTR)_2Cob$. However, compounds or complexes of other stoichiometries are within the scope of this invention.

The reaction between NHTR and Ad-Cob can be carried out in ethanol solution or in other lower alcohols at amibent or slightly elevated temperatures. The product need not be isolated and can be taken up in an suitable vehicle for administration, for example, propylene glycol, by adding propylene glycol to an ethanolic solution of N-homocysteine thiolactonyl retinamido cobalamin and removing ethanol under reduced pressure.

N-Homocysteine thiolactonyl retinamido cobalamin can be characterized by its ultraviolet-visible absorption spectrum, between 200 and 800 nm. This spectrum, as shown on FIG. 1, differs from that of either of the precursor compounds. In FIG. 2 is shown the ultraviolet-visible differential absorption spectra, determined by the difference between the spectra of $(NHTR)_2$-Cob and Ad-Cob, in the 200–700 nm range.

It is proposed that NHTR displaces 5'-deoxyadenosine, coordinated to Co in the coenzyme $B_{12}$ molecule. Increased absorption of N-homocysteine thiolactonyl retinamido cobalamin between 600 and 800 nm and the spectral differences between this substance and the starting materials indicate formation of a complex in which N-homocysteine thiolactonyl retinamide is bonded to the cobalt atom of cobalamin. It appears that the 5'-deoxyadenosyl ligand is displaced during formation of this complex. The absorption maximum at 640 nm corresponds to a complex formed at a 2:1 molar ratio of NHTR to Cob (FIG. 3), which is a preferred compound of this invention. Maximumization of absorption at 640 nm suggests that the ligand occupies both axial positions of the octahedral complex of cobalamin.

N-Homocysteine thiolactonyl retinamido cobalamin has been found effective for reducing induction of pulmonary tumors by a chemical carcinogen, ethyl carbamate. Despite its efficacy in reducing tumor induction, N-homocysteine thiolactonyl retinamido cobalamin has relatively low toxicity. In this respect, the compound of this invention is superior to many known antineoplastic agents, which have cumulative toxicity after prolonged administration, conventional in cancer chemotherapy. The compound is therefore useful for chemoprevention and chemotherapy of malignant neoplasms in animals.

It has further been found that N-homocysteine thiolactonyl retinamido cobalamin inhibits weight gains in animals treated therewith. The compound can therefore be used as an agent for inhibiting weight gain, without otherwise affecting the animal being treated. It is proposed that weight gain is inhibited because animals to which N-homocysteine thiolactonyl retinamido cobalamin is administered become more active than control animals.

It is proposed that N-homocysteine thiolactonyl retinamido cobalamin prevents the formation of malignant cells in experimental animals by preventing depletion of methionine from normal tissues by chemical carcinogens. In view of the relationship between carcinogenesis and atherogenesis, it is expected that N-homocysteine thiolactonyl retinamido cobalamin will also be useful for preventing atherosclerosis by preventing the accumulation of homocysteine thiolactone, which causes formation of atherosclerotic plaques in arteries.

Due to its tumor inhibiting activity, the compound of this invention is useful as an antineoplastic or chemopreventive agent in human and veterinary medicine.

The compound of this invention can be used in admixture with conventional excipients, i.e. pharmaceutically and physiologically acceptable organic or inorganic carriers suitable for enteral, parenteral or topical applications which do not deleteriously interact with the active compounds.

Suitable pharmaceutically and physiologically acceptable carriers include, but are not limited to, water, salt solutions, alcohols, glycols, vegetable oils, polyethylene glycols, gelatin, lactose, amylose, magnesium stearate, talc, silicic acid, viscous paraffin, perfume oil, fatty acid monoglycerides and diglycerides, pentaerythritol fatty acid esters, hydroxymethyl cellulose, polyvinyl pyrrolidone, etc. The pharmaceutical preparations can be sterilized and, if desired, mixed with auxiliary agents, including lubricants, preservatives, stabilizers, wetting agents, emulsifiers, salts for influencing osmotic pressure, buffers, coloring, flavoring and/or aromatic substances and the like which do not deleteriously interact with the active compound.

Solutions, preferably glycol, oil or alcohol solutions, as well as suspensions, emulsions or implants, including suppositories, can be used for parenteral application. Unit dosages can conveniently be provided in ampoules. It is preferred to administer the active compound intraperitoneally in the form of a solution in propylene glycol.

It will be appreciated that the actual preferred amount of active compound used will vary according to the specific isomer being used, the particular compositions formulated, the mode of application and particular site and organism being treated. Optimal application rates for a given set of conditions can be ascertained by those skilled in the art using conventional dosage determination tests in view of the above guidelines.

BEST MODE FOR CARRYING OUT THE INVENTION

In a most preferred aspect, the compound of this invention corresponds to the formula $(NHTR)_2Cob$ and the retinamide function is all-trans.

In a preferred method of use, tumors are those induced by ethyl carbamate, the compound is $(NHTR)_2Cob$ and the retinamide function is all-trans.

Without further elaboration it is believed that one skilled in the art can, using the preceding description, utilize the present invention to its fullest extent. The following preferred specific embodiments are, therefore, to be construed as merely illustrative and not limitative of the reminder of the disclosure in any way whatsoever.

In the following examples, temperatures are set forth uncorrected in degrees Celsius. Unless otherwise indicated, all parts and percentages are by weight.

EXAMPLE 1

Preparation of N-Homocysteine Thiolactonyl Retinamido Cobalamin

N-Homocysteine thiolactonyl retinamide (10 gm, all-trans, McCully '685) was dissolved in 100 mL of ethanol with stirring at 37° C. To the resulting solution was added 20 mg of 5'-deoxyadenosyl cobalamin (coenzyme $B_{12}$, Sigma Chemical Co., St. Louis, Mo.). In some experiments, 0.005 mL of conc HCl was added to prevent precipitation of Ad-Cob. The resulting mixture was protected from light during the gradual formation of a clear, salmon pink solution at 37° C. The product was transferred to a non-volatile, non-toxic solvent (propylene glycol) by adding 20 mL of propylene glycol to the ethanolic solution and removing ethanol under reduced pressure at 37° C.

Figure 1:
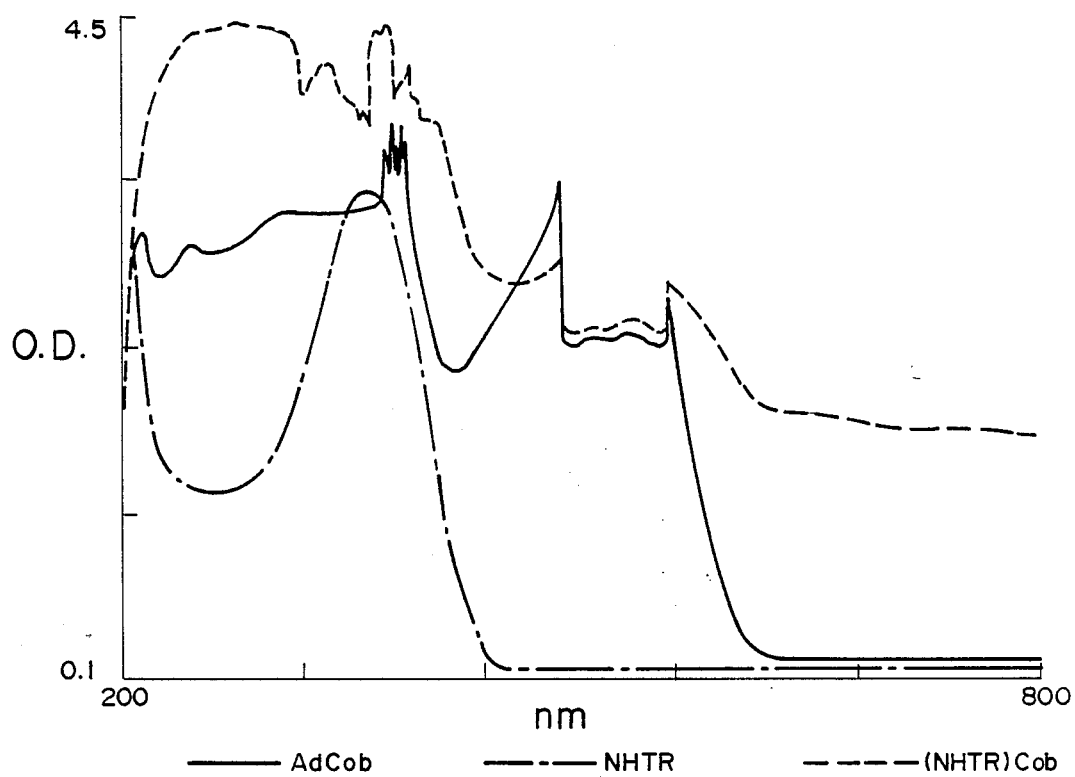
In FIG. 1 is shown the ultraviolet-visible absorption spectrum of a compound of this invention.
Figure 2:
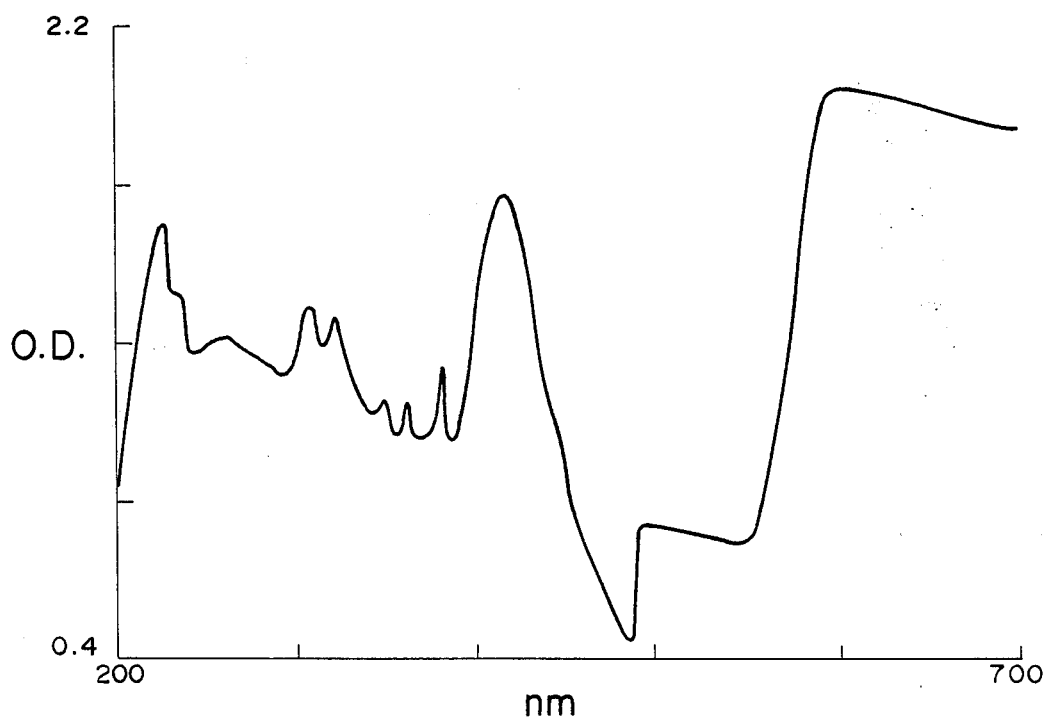
In FIG. 2 is shown a differential ultraviolet-visible spectrum of a compound of this invention.
Figure 3:
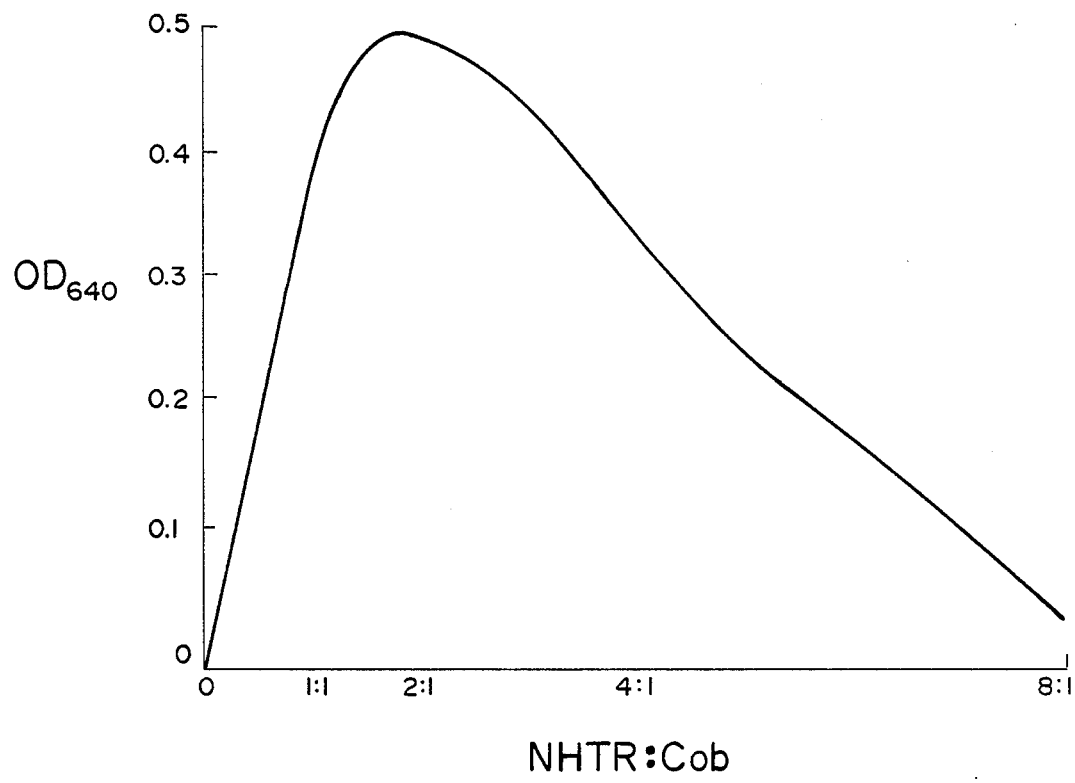
In FIG. 3 is shown a plot of absorption ot 640 nm, as a function of NHTR:Cob ratios.

Ultraviolet visible absorption spectra of N-homocysteine thiolactonyl retinamide cobalamin [$(NHTR)_3Cob$] and its precursors, N-homocysteine thiolactonyl retinamide (NHTR) and 5'-deoxyadenosyl cobalamin (Ad-Cob) in propylene glycol at pH 2 were obtained on a Beckman Model DU-7 spectrophotometer, equipped for computerized data analysis. Spectra are shown in FIG. 1.

EXAMPLE 2

Effect of N-Homocysteine Thiolactonyl Retinamido Cobalamin and Precursors on Urethane-induced Pulmonary Tumors in Mice Solutions of $(NHTR)_2Cob$ in propylene glycol (PG), prepared as in Example 1, or of Ad-Cob in PG or NHTR in PG, were injected intraperitoneally into A/J female mice (15-20 g) weekly for 16 weeks. On the day before each of the first 10 weekly injections of test compound, ethyl carbamate (2 mg in 0.2 mL of water) was injected intraperitoneally for a total dose of 20 mg of ethyl carbamate per animal. The mice were weighed at weekly intervals. At the end of 16 weeks, the mice were sacrificed. The lungs were dissected, fixed in 10% neutral buffered formalin and examined under a dissecting microscope for tumors. No difference in tumor diameters was observed. Values for P for differences between experimental and control animals were determined using the student t test. The following results were obtained:

| Compound | PG | $(NHTR)_2Cob$ | Ad-Cob | NHTR |
|---|---|---|---|---|
| Total dose (mg/kg) | — | 60 | 40 | 20 |
| Survivors/total | 20/20 | 21/21 | 20/20 | 20/20 |
| Weight gain (g + SE) | 5.9 ± 0.15 | 3.8 ± 0.53 | 4.8 ± 0.25 | 5.3 ± 0.53 |
| P (weight gain | — | 0.01 | 0.01 | NS |
| Tumors/animal | 7.5 ± 0.75 | 5.6 ± 0.72 | 9.8 ± 0.23 | 6.9 ± 1.10 |
| P (tumors) | — | 0.045 | 0.0008 | NS |

The results show that N-homocyteine thiolactonyl retinamido cobalamin decreased the number of pulmonary tumors, induced in A/J mice by ethyl carbamate. N-Homocysteine thiolactonyl retinamide alone had no significant effect on urethane-induced pulmonary tumors at the dose given. 5'-Deoxyadenosyl cobalamin promoted the number of pulmonary tumors induced. Both N-homocysteine thiolactonyl cobalamin and 5'-adenosyl cobalamin significantly decreased weight gain. No abnormalities, other than pulmonary tumors, were observed at autopsies of any of the mice.

EXAMPLE 3

Determination of Toxicity of N-Homocysteine Thiolactonyl Retinamido Cobalamin

Injections of 0.1 mL of a solution of N-homocysteine thiolactonyl retinamido cobalamin (2:1, as in Example 1) in propylene glycol (0.1 mg/mL) were made intraperitoneally in female A/J mice at weekly intervals for 9 weeks. No carcinogen was administered. The mice were weighed at weekly intervals and observed for 10 weeks after the treatment period. Autopsies of the animals at week 19 revealed no abnormalities, other than scattered peritoneal adhesions. During weeks 1-9, the test mice were very active and restless. The following results were measured:

| | |
|---|---|
| Dose of $(NHTR)_2Cob$ (mg/kg/week) | 5 |
| Total dose (mg/kg) | 45 |
| Weeks treated | 9 |
| Weeks observed after treatment | 10 |
| Survivors/total | 5/5 |
| Weight gain (treatment period) | −1.6 g |
| Weight gain (observed period) | +5.0 g |

The results show that $(NHTR)_2Cob$, at a weekly dose of 5 mg/kg for 9 weeks, was tolerated without any fatalities. Weight gain was completely inhibited during this period. For 10 weeks after the treatment period, the test animals gained weight normally and became less active.

EXAMPLE 4

Effect of N-Homocysteine Thiolactonyl Retinamido Cobalamin and Precursors on Pulmonary Tumors in Mice, Induced by a Single Dose of Ethyl Carbamate Experiments were done, as in Example 2, except that ethyl carbamate was administered in a single dose, rather than in ten weekly doses. As shown by the results in Table 1, many more pulmonary tumors were induced. N-Homocysteine thiolactonyl retinamido cobalamin also significantly inhibited tumor formation under these conditions.

EXAMPLE 5

Effect of NHTR:Cob Ratios on Ultraviolet Absorption at 640 nm

Complexes of NHTR-Cob were made as in Example 1, except that the ratio of HNTR:Cob was varied. Absorption of the resulting complexes was measured at 640 nm. Maximum absorption was observed for a complex, corresponding to the formula $(NHTR)_2Cob$.

described reactants and/or operating conditions of this invention for those used in the preceding examples.

From the foregoing description, one skilled in the art can easily ascertain the essential characteristics of this invention and, without departing from the spirit and scope thereof, can make various changes and modifications of the invention to adapt it to various usages and conditions.

I claim:

1. The compound homocysteine thiolactonyl retinamido cobalamin trans isomer characterized by the formula $(NHTR)_2Cob$, wherein NHTR is N-homocysteine thiolactonyl retinamide and Cob is cobalamin wherein the ultraviolet-vsible spectrum is represented by FIG. 1 with an absorption maximum at 640 nm.

2. A process for preparing the compound of claim 1, comprising reacting N-homocysteine thiolactonyl retinamide with 5'-desoxyadenosyl cobalamin and wherein about two moles of N-homocysteine thiolactonyl retinamide are reacted with each mole of 5'-desoxyadenosyl cobalamin.

3. A method for decreasing the induction of chemically-induced tumors in animals, comprising administering to an animal being treated a compound of claim 1, in

TABLE 1

Effect of N-Homocysteine Thiolactonyl Retinamido Cobalamin on Mice, Treated with a Single Large Dose of Ethyl Carbamate

| Group | Compound | Total Dose (mg/kg) | Survivors/total | Weight gain (g ± SE) | P | Tumors/animal (number ± SE) | P |
|---|---|---|---|---|---|---|---|
| 1 | — | — | 20/20 | 8.5 ± 0.75 | — | 26.7 ± 1.29 | — |
| 2 | vehicle | — | 19/20 | 7.5 ± 0.70 | NS | 27.0 ± 1.03 | — |
| 3 | $(NHTR)_2Cob$ | 0.75 | 17/20 | 6.5 ± 0.61 | NS | 22.2 ± 1.61 | 0.01 |
| 4 | $(NHRT)_2Cob$ | 7.5 | 16/20 | 6.0 ± 0.88 | NS | 17.4 ± 1.71 | 0.001 |
| 5 | $(NHTR)_2Cob$ | 22.5 | 6/20 | 5.7 ± 2.76 | NS | 14.0 ± 1.76 | 0.0000001 |
| 6 | $(NHTR)_2Cob$ | 30 | 3/20 | 5.4 | — | 17.7 ± 1.20 | 0.006 |
| 7 | Ad-Cob | 5.0 | 12/20 | 7.1 ± 0.50 | NS | 24.0 ± 1.44 | NS |
| 8 | NHTR | 2.5 | 12/20 | 7.1 ± 0.90 | NS | 25.9 ± 1.70 | NS |
| 9 | NHTR + Ad-Cob | 2.5 5.0 | 14/20 | 8.1 ± 1.70 | NS | 26.2 ± 1.70 | NS |

Aqueous solutions (0.5 mL) of 20 mg of ethyl carbamate were injected intraperitoneally into A/J female mice (15–18 g) on day one. Four hours later, 0.1 mL of propylene glycol, containing $(NHTR)_2Cob$, was injected into group 6. On day two, 0.1 mL of propylene glycol containing $(NHTR)_2Cob$, Ad-Cob or NHTR, was injected into groups 3–9. On day four, $(NHTR)_2Cob$ and Ad-Cob were injected into groups 5,6 and 9. Group 9 received NHTR on day two and Ad-Cob on day four.
$(NHTR)_2Cob$ was administered to groups 5 and 6 on day six.
Fatalities occured as follows:
Group 2: week 12
Group 3: day 6 (2) and week 9
Group 4: day 6, day 8, week 8 and week 10
Group 5: day 6 (4), day 7 (2), day 8 (4), day 9, day 10 (3)
Group 6: day 3, day 6 (2), day 7 (4), day 9 (4), day 10, day 11 (2) and day 13 (3)
Group 7: day 6 (2), day 7, day 8, day 9 (2), week 9, week 10
Group 8: day 6 (4), day 8 (2), day 13 and week 5
Group 9: day 6 (3), day 7 (2) and day 8
Body weight was recorded weekly and average weights were determined from initial and final weights. After 16 weeks, the animals were sacrified and the lungs were dissected and fixed in formalin. Tumors were counted and the diameters were measured. No differences in tumor diameters were observed.
SE = standard error
NS = not significant The compounds herein disclosed and claimed have been found effective in diminishing the number of chemically-induced tumors in laboratory mice. Based on studies with laboratory animals it may be possible, through further study, to find that the compounds have value as a therapeutic agent in the treatment and prevention of human cancer. It may also be possible to demonstrate the use of this compound to prevent and treat human atherosclerosis.

The preceding examples can be repeated with similar success by substituting the generically or specifically admixture with a physiologically and pharmaceutically acceptable carrier, in an amount effective to decrease induction of tumors.

4. The method of claim 3, wherein the tumors are induced by ethyl carbamate.

5. A method for inhibiting weight gain in animals, comprising administering to an animal being treated a compound of claim 1 in admixture with a physiologically and pharmaceutically acceptable carrier, in an amount effective to inhibit weight gain.

* * * * *